(12) United States Patent
Itoi (10) Patent No.: US 7,744,539 B2
(45) Date of Patent: Jun. 29, 2010

(54) ULTRASONIC ENDOSCOPE

(75) Inventor: Hiromu Itoi, Saitama (JP)

(73) Assignee: Fujinon Corporation, Saitama (JP)

( * ) Notice: Subject to any disclaimer, the term of this patent is extended or adjusted under 35 U.S.C. 154(b) by 644 days.

(21) Appl. No.: 11/392,707

(22) Filed: Mar. 30, 2006

(65) Prior Publication Data

US 2006/0241481 A1 Oct. 26, 2006

(30) Foreign Application Priority Data

Mar. 31, 2005 (JP) ............................ P.2005-100552

(51) Int. Cl.
*A61B 8/00* (2006.01)
(52) U.S. Cl. .................. 600/459; 600/101; 600/407; 600/437; 600/446; 600/447; 600/462; 600/463
(58) Field of Classification Search .................. 600/433, 600/459–472, 101, 407, 437, 446, 447
See application file for complete search history.

(56) References Cited

U.S. PATENT DOCUMENTS 5,091,893 A * 2/1992 Smith et al. .................. 367/153
5,493,541 A * 2/1996 Snyder ....................... 367/155

2001/0041841 A1 11/2001 Ohara et al.
2002/0062083 A1 5/2002 Ohara et al.
2005/0143659 A1* 6/2005 Saiga ......................... 600/463

FOREIGN PATENT DOCUMENTS

JP 2001-314403 A 11/2001
WO WO-03/011139 A1 2/2003

* cited by examiner

*Primary Examiner*—Long V Le
*Assistant Examiner*—Vani Gupta
(74) *Attorney, Agent, or Firm*—Birch, Stewart, Kolasch & Birch, LLP (57) ABSTRACT

A distal hard part in an insertion portion is provided with an ultrasonic transducer in which a large number of ultrasonic vibrators are arranged in the circumferential direction. The ultrasonic transducer is shaped like a cylinder. Each member that constitutes an endoscopic observation section is passed through this tunnel-like passage. Each ultrasonic vibrator is provided with a single common electrode and individual electrodes the number of which corresponds to the number of the ultrasonic vibrators. Flexible boards and are provided on the proximal and distal end sides of the ultrasonic transducer. Wires are connected to these flexible boards. The wires from the flexible board are extended without changes, whereas the wires from the flexible board are reversely turned from the distal end side, are then passed through the tunnel-like passage, and are extended in the direction of an angle part.

4 Claims, 12 Drawing Sheets

ULTRASONIC ENDOSCOPE

BACKGROUND OF THE INVENTION

1. Field of the Invention

The present invention relates to an ultrasonic endoscope in which an endoscopic observation section that has an observation visual field ahead of a distal hard part of an insertion portion and an electronic scanning type ultrasonic transducer that has a circumferential or circularly arcuate ultrasonic scan surface perpendicular to an axial line of the distal hard part are attached to the distal hard part.

2. Description of the Related Art

An ultrasonic endoscope has a structure in which an endoscopic observation means and an ultrasonic transducer are attached to a distal hard part of an insertion portion that is inserted into, for example, a body cavity. As a scanning manner by this ultrasonic transducer, a so-called electronic scanning type ultrasonic transducer in which a large number of ultrasonic vibrators are arranged in a predetermined direction, and are sequentially driven is widely used in the related art. For example, JP-A-2001-314403 describes a direct-view endoscope in which an area in front of the distal hard part of the insertion portion is observed as an observation visual field in the endoscopic observation means, and an ultrasonic scan surface by the ultrasonic transducer is made to be radial, i.e., circumferential or arcuate within a predetermined angular range.

The ultrasonic endoscope disclosed by this JP-A-2001-314403 is inserted into, for example, body cavity tubes, i.e., upper alimentary canals, such as the esophagus and the duodenum, or lower alimentary canals, such as the large intestine, so that a forward area in the insertion direction is observed by the endoscopic observation means. As a result, if a region of interest, such as diseased parts, is detected, the ultrasonic transducer is positioned to face this region of interest, whereby information on body tissues of the region can be obtained.

Herein, wires are respectively connected to ultrasonic vibrators, which constitute the ultrasonic transducer, in the ultrasonic transducer. However, it is difficult to connect these wires directly to the ultrasonic vibrators. Therefore, in general, flexible boards are connected to the ultrasonic vibrators arranged in the circumferential direction, and terminal parts the number of which corresponds to the number of ultrasonic vibrators are formed on the flexible boards, and then the wires are connected to the terminal parts by, for example, a soldering means.

As described above, a large number of ultrasonic vibrators are arranged in the circumferential direction if the ultrasonic scan surface is in the radial direction. However, to heighten the resolution of an ultrasonic tomographic image, the number of ultrasonic vibrators is increased. From the viewpoint of making the diameter of the insertion portion smaller, the area of the flexible board cannot be widened. Therefore, in the flexible board, the distance between the terminals becomes close even if the wire-connecting terminals are zigzag arranged as a possible design. As a result, it becomes difficult to connect the wires to the terminals, and there is a possibility that connection strength will be weakened. Additionally, there is a possibility that, for example, a short circuit is disadvantageously caused by allowing solder to overflow from the terminal part.

SUMMARY OF THE INVENTION

The present invention has been made in consideration of the foregoing circumstances. It is therefore an object of the present invention to electrically connect ultrasonic vibrators that constitute an ultrasonic transducer and wires together easily and stably.

To achieve the object, according to the present invention, there is provided an ultrasonic endoscope comprising an insertion portion comprising: an angle part; a distal hard part; a cylindrical body that connects the angle part and the distal hard part; an ultrasonic transducer attaching portion formed annularly; an endoscopic observation section attaching portion including a lighting portion and an observation portion, the lighting portion and the observation portion passing through an inside of the ultrasonic transducer attaching portion and facing a front edge surface of the distal hard part; an ultrasonic transducer in which a plurality of ultrasonic vibrators are arranged like a cylinder or like a circular arc so as to perform ultrasonic electronic scanning in a circumferential direction, the ultrasonic transducer being attached to the ultrasonic transducer attaching portion; a first flexible board connected to a distal end side of the ultrasonic transducer attaching portion, a second flexible board connected to a proximal end side of the ultrasonic transducer attaching portion, wherein the first flexible board comprises connection parts to electrodes of ones of the ultrasonic vibrators, the second flexible board comprises connection parts to electrodes of the other ones of the ultrasonic vibrators, each of the first and second flexible boards comprises a predetermined number of wire connection parts, wires are connected to each of the wire connection parts, those of the wires connected to the second flexible board are extended as they are, and the first flexible board or those of the wires connected to the first flexible board are extended toward the angle part through a hollow part of the ultrasonic transducer attaching portion.

Herein, a difference in the number of the wire connection parts can be made in both flexible boards although the flexible-board on the proximal end side and the flexible board on the distal end side can have the same number of connection parts. In this case, the wires connected to the flexible board on the distal end side undergo a turnabout from the forward side, and are drawn out toward the angle part through a hollow part of the ultrasonic transducer attaching portion. Therefore, the flexible board on the distal end side is inferior in the drawing-around condition to the flexible board on the proximal end side where the wires are drawn out toward the angle part without changes. Additionally, not only the wires from the ultrasonic vibrators but also members connected to the endoscope, such as signal cables from a light guide or a solid-state image pickup element and a treatment-instrument insertion channel, are passed through the inside of the hollow part in the ultrasonic transducer attaching portion. Therefore, a space used to pass the wires through the hollow part is restricted. For this reason, the number of the wires connected to the flexible board on the distal end side can be reduced. In other words, the second flexible board is greater in number of the connection parts to the electrodes of the ultrasonic vibrators than the first flexible board. With regard to how to distribute the wires, regular distribution can be performed. For example, two adjoining electrodes of the ultrasonic vibrator are connected to the flexible board on the proximal end side, and a single electrode of the ultrasonic vibrator subsequent thereto is connected to the flexible board on the distal end side. Alternatively, from the positional relationship between the position of the ultrasonic vibrator and the position of another member, the wires can be distributed to the flexible board on the proximal end side and the flexible board on the distal end side so as to avoid mutual interference.

DETAILED DESCRIPTION OF THE INVENTION

Figure 1:
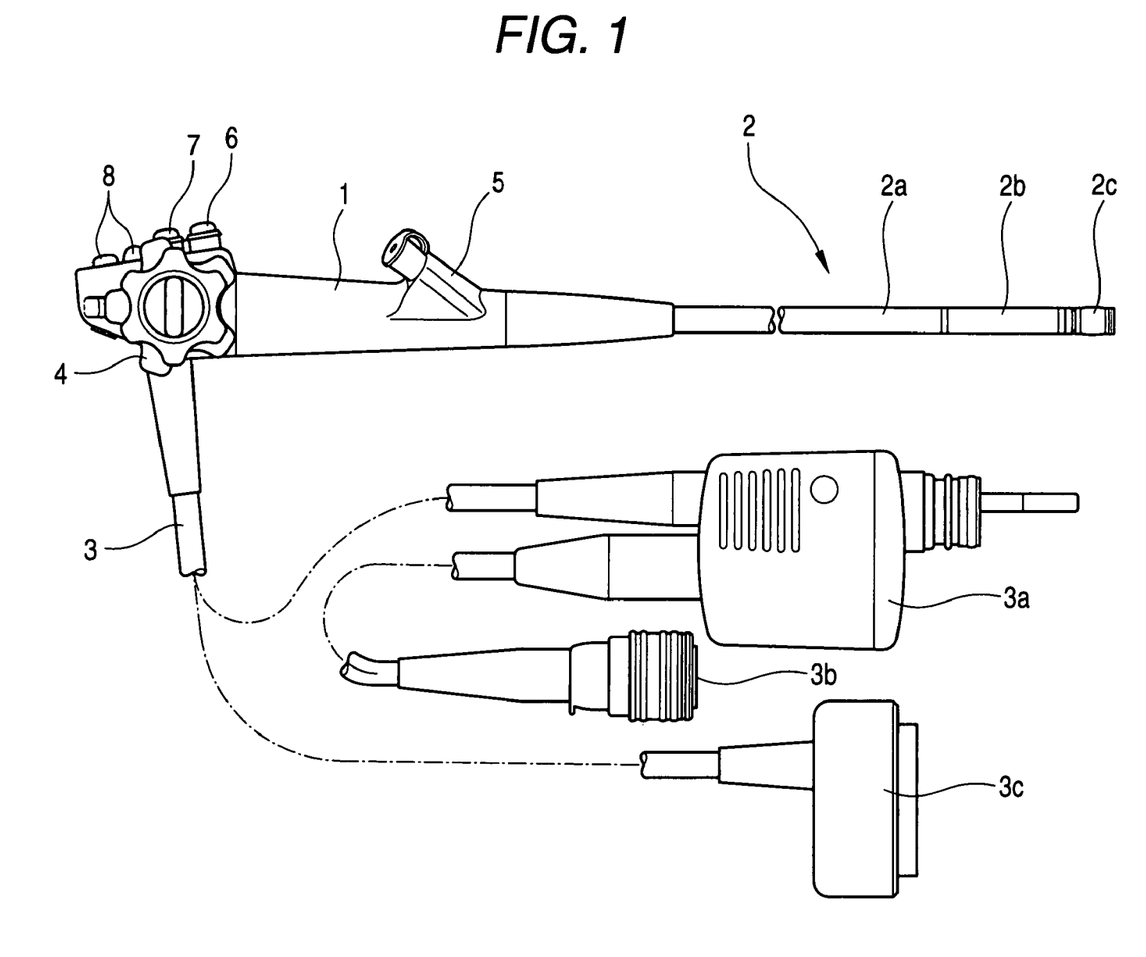
FIG. 1 is a general schematic view of an ultrasonic endoscope that shows one embodiment of the present invention.

An embodiment of the present invention will be hereinafter described in detail with reference to the attached drawings. First, as shown in FIG. 1, an ultrasonic endoscope is roughly made up of a main control portion 1, an insertion portion 2, and a universal cord 3. A light source device, a video signal processor, and an ultrasonic wave observation device are connected to the ultrasonic endoscope, thus constituting a system as a whole. The universal cord 3 includes a connector 3a that is drawn out of the main control portion 1, then branches off in the middle thereof, and is detachably connected to the light source device, a connector 3b that is detachably connected to the video signal processor, and a connector 3c that is detachably connected to the ultrasonic wave observation device.

The main control portion 1 can be gripped by, for example, one hand of an operator, and is provided with an angle operating section 4 and a treatment-equipment introducing portion 5. The main control portion 1 is further provided with operating buttons, such as an air/water supply button 6 and a suction button 7, and various switches 8.

The insertion portion 2 is a code-like member that has a predetermined length and that is connected to the main control portion 1. The insertion portion 2 is inserted into, for example, the body of a subject. The insertion portion 2 is made up of a flexible part 2a, an angle part 2b, and a distal hard part 2c. The flexible part 2a occupies most of the length from a connection part to the main control portion 1, and is freely bent along an insertion path in a body cavity or the like. The angle part 2b is connected to an end of the flexible part 2a. The distal hard part 2c is connected to the angle part 2b. To direct the distal hard part 2c in a desired direction, the angle part 2b can be operated to be bent upwardly, downwardly, leftwardly, and rightwardly by remote control. Therefore, the angle operating section 4 is mounted on the main control portion 1. The angle part 2b is bent by the operation of an operator, and is controlled to direct the distal hard part 2c in a desired direction.

Figure 2:
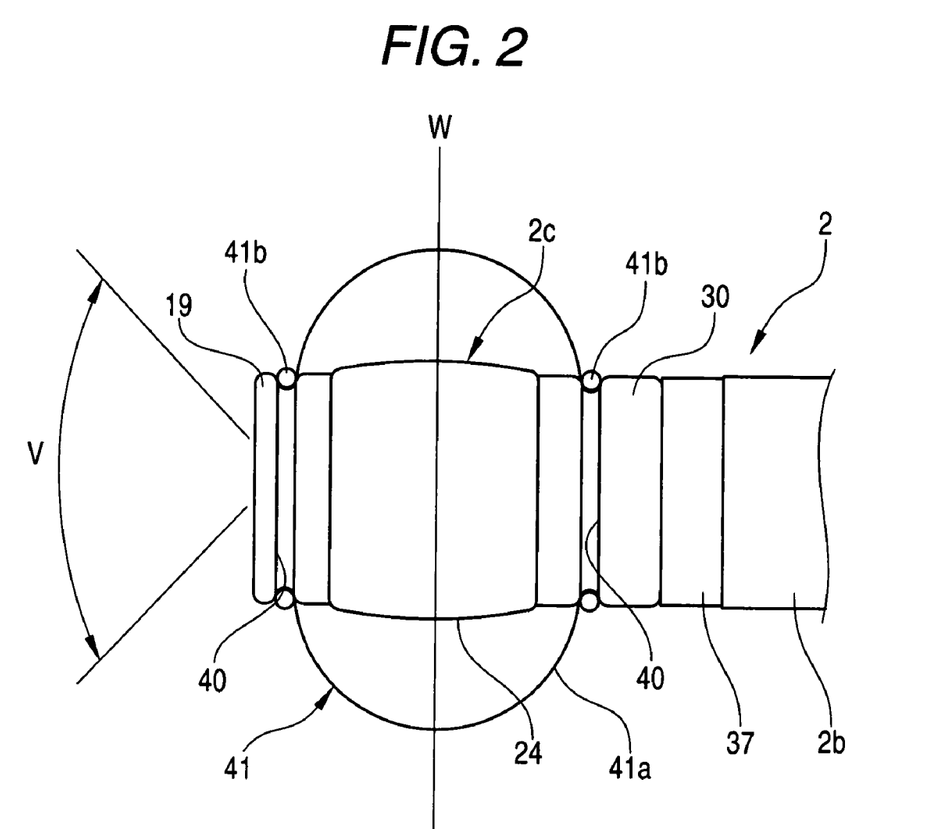
FIG. 2 is an external view of the distal end of an insertion portion.
Figure 3:
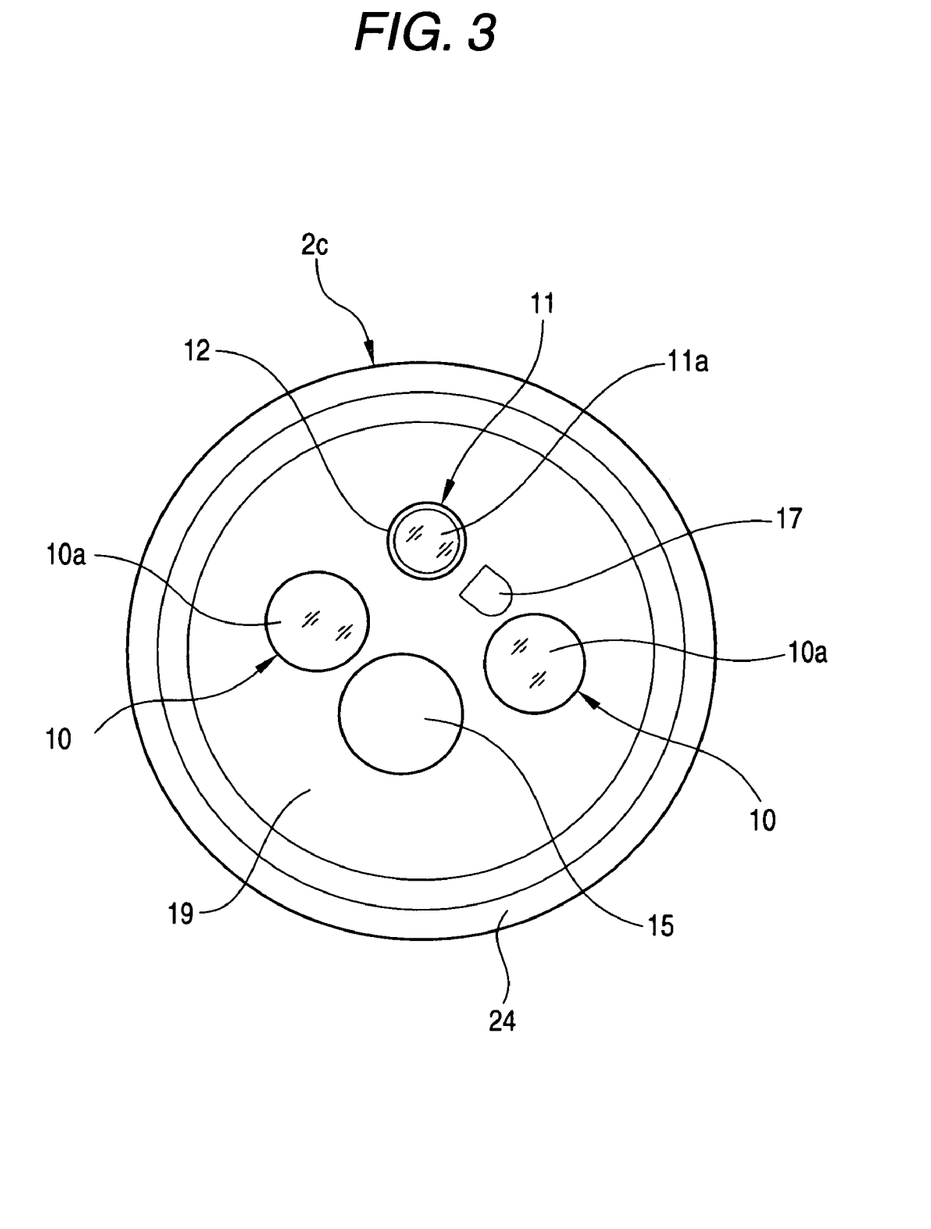
FIG. 3 is a view showing the forward end surface of a distal hard part.

FIG. 2 shows a tip part of the insertion portion 2, and FIG. 3 shows a structure of an end surface of the distal hard part 2c of the insertion portion 2. As is apparent from these figures, the distal hard part 2c is provided with an endoscopic observation section and an electronic radial scan type ultrasonic transducer. The endoscopic observation section has a visual field in a direction of an extension line of its axial line, i.e., forward of the distal hard part 2c, and has a predetermined visual angle V. The electronic radial scan type ultrasonic transducer has a circular or circularly arcuate ultrasonic scan surface W at a position closer to the proximal end than the visual field of the endoscopic observation section.

Figure 4:
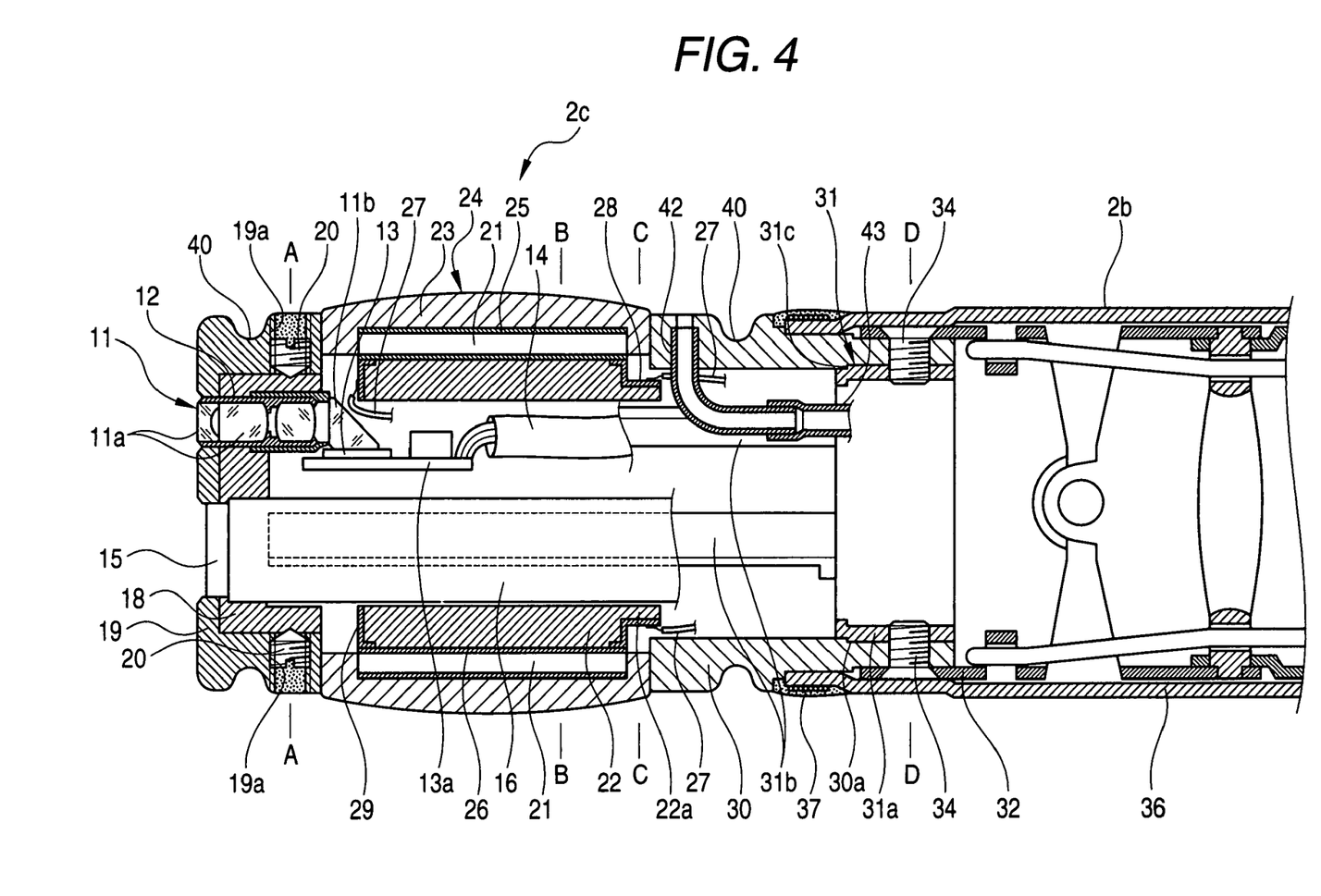
FIG. 4 is a longitudinal sectional view of the distal hard part.

FIG. 4 is a cross-sectional view of the tip part of the insertion portion 2. As is apparent from this figure and FIG. 3, the endoscopic observation section is made up of a plurality of lighting portions 10 and an observation portion 11. The lighting portions 10 are disposed at both side positions, respectively, with the observation portion 11 therebetween. The lighting portion 10 includes a lighting lens 10a, which faces the end surface of the distal hard part 2c, and a light guide 10b (see FIG. 5 to FIG. 8). The light guide 10b is made of a large number of bundles of extra-fine optical fibers, and is extended from the connector 3a of the universal cord 3 to the distal hard part 2c of the insertion portion 2. An illumination light emitting end of the light guide 10b is positioned to face the lighting lens 10a. On the other hand, the observation portion 11 is made up of an objective lens 11a and a prism 11b by which an optical path from the objective lens 11a is bent by 90°. The objective lens 11a is disposed in a lens tube 12, and the prism 11b is fixed to the lens tube 12. A solid-state image pickup element 13 is joined to the prism 11b. A predetermined number of signal lines are connected to a substrate 13a of the solid-state image pickup element 13. The signal lines are bundled into a single video cable, and are extended to the connector 3b of the universal cord.

A treatment equipment lead-out opening 15 used to outwardly lead forceps and other pieces of treatment equipment is further provided at the end surface of the distal hard part 2c of the insertion portion 2. A connection pipe 16, to which a treatment-equipment passing tube from the treatment-equipment introducing portion 5 mounted on the main control portion 1 is connected, is attached to the treatment equipment lead-out opening 15. The treatment-equipment passing tube is formed so as to be joined with a suction path inside the main control portion 1. Further, a nozzle 17 used to wash the objective lens 12 when the end surface of the objective lens 12 of the observation portion 11 is stained with body fluids or the like is attached to the distal hard part 2c. A fluid supply tube 9 for washing which is operated by the air/water supply button 6 (see FIG. 5 to FIG. 8) is connected to the nozzle 17.

Figure 5:
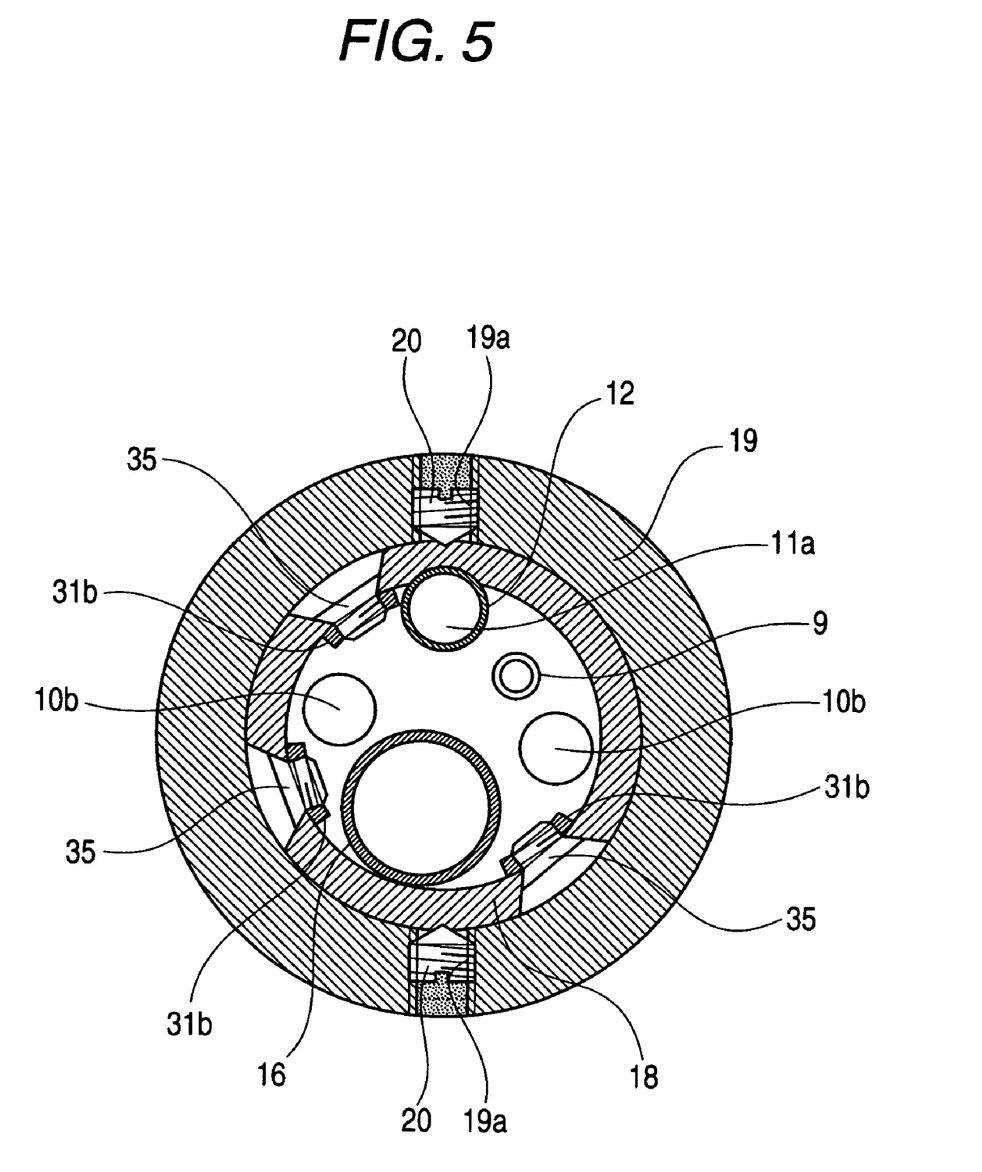
FIG. 5 is a sectional view along line A-A of FIG. 4.
Figure 6:
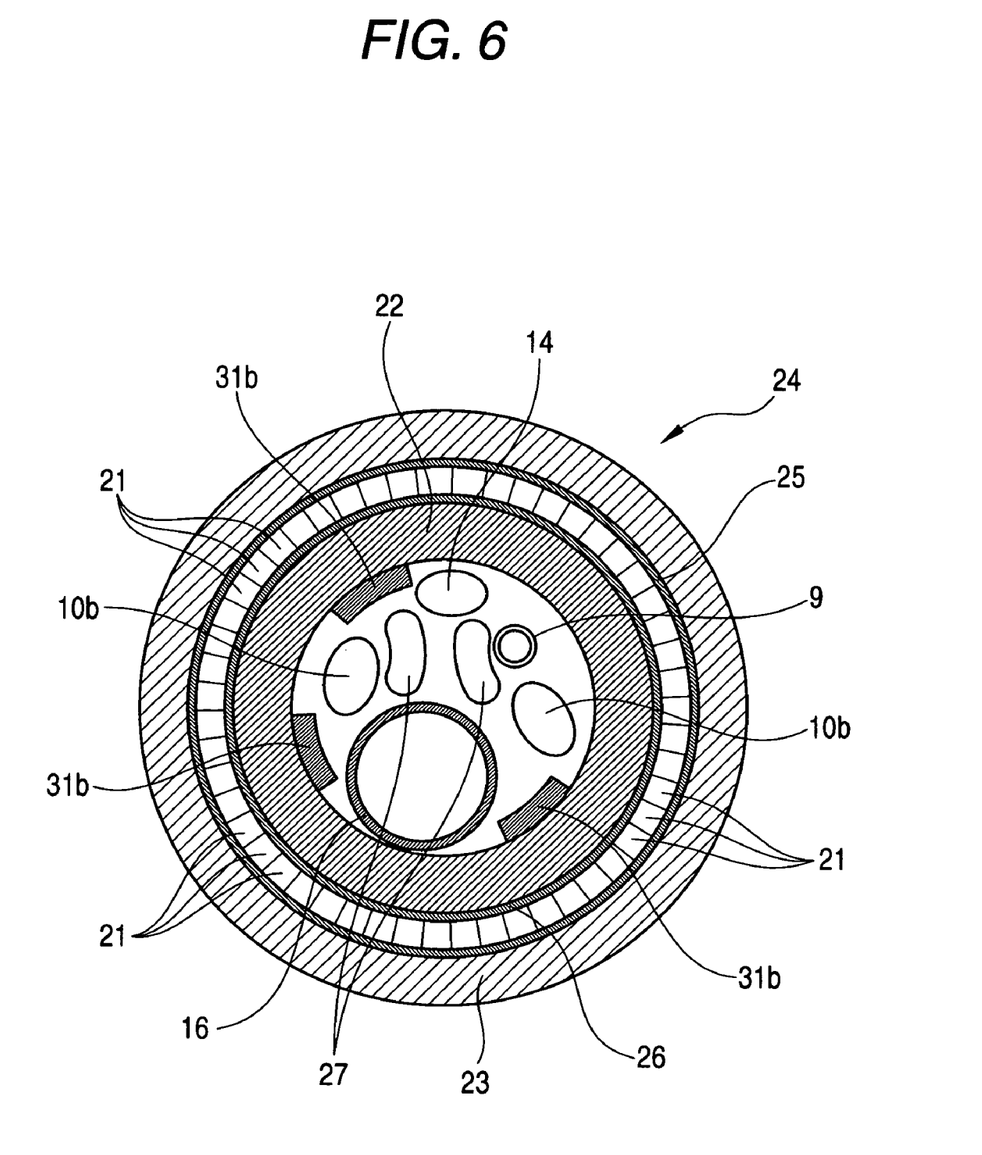
FIG. 6 is a sectional view along line B-B of FIG. 4.
Figure 7:
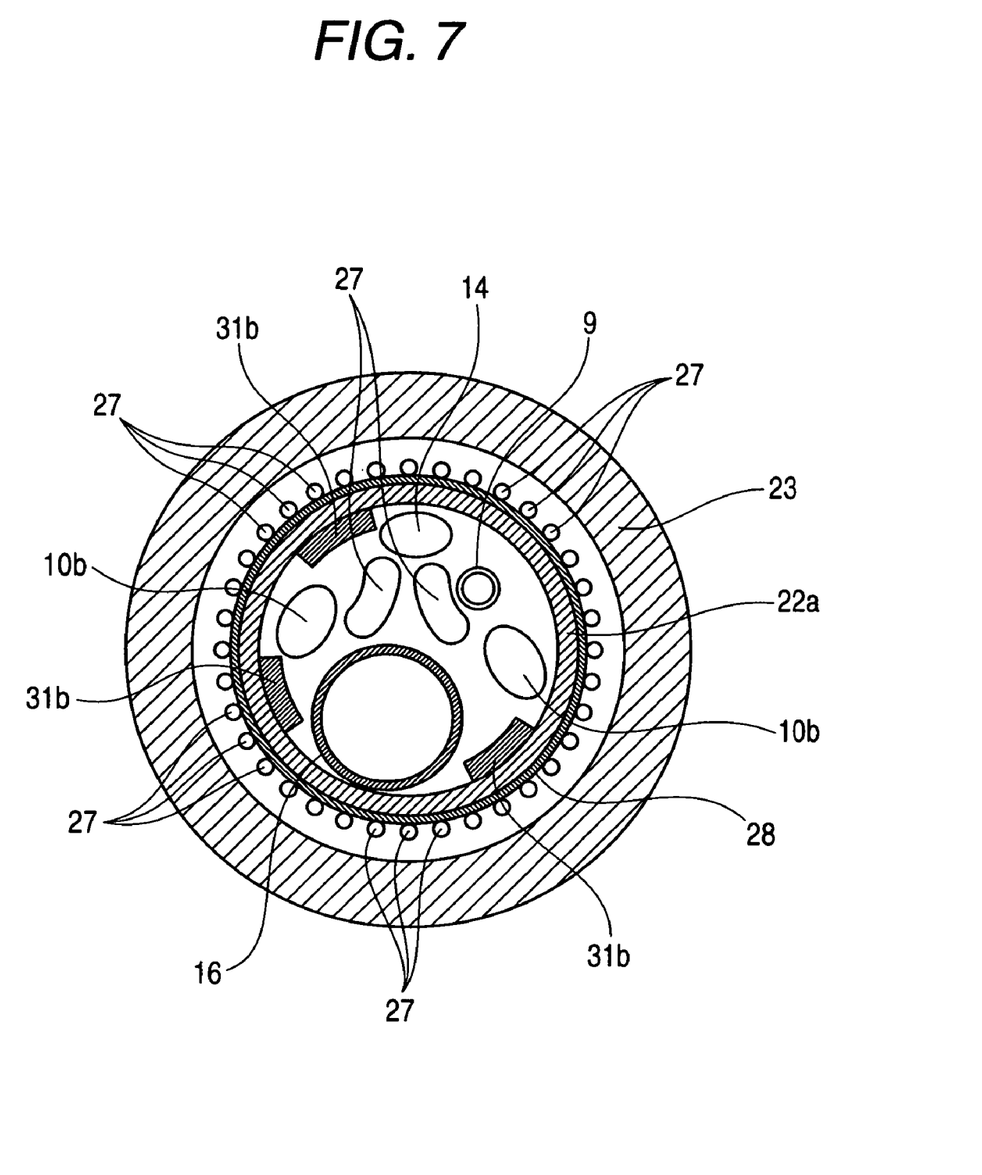
FIG. 7 is a sectional view along line C-C of FIG. 4.
Figure 8:
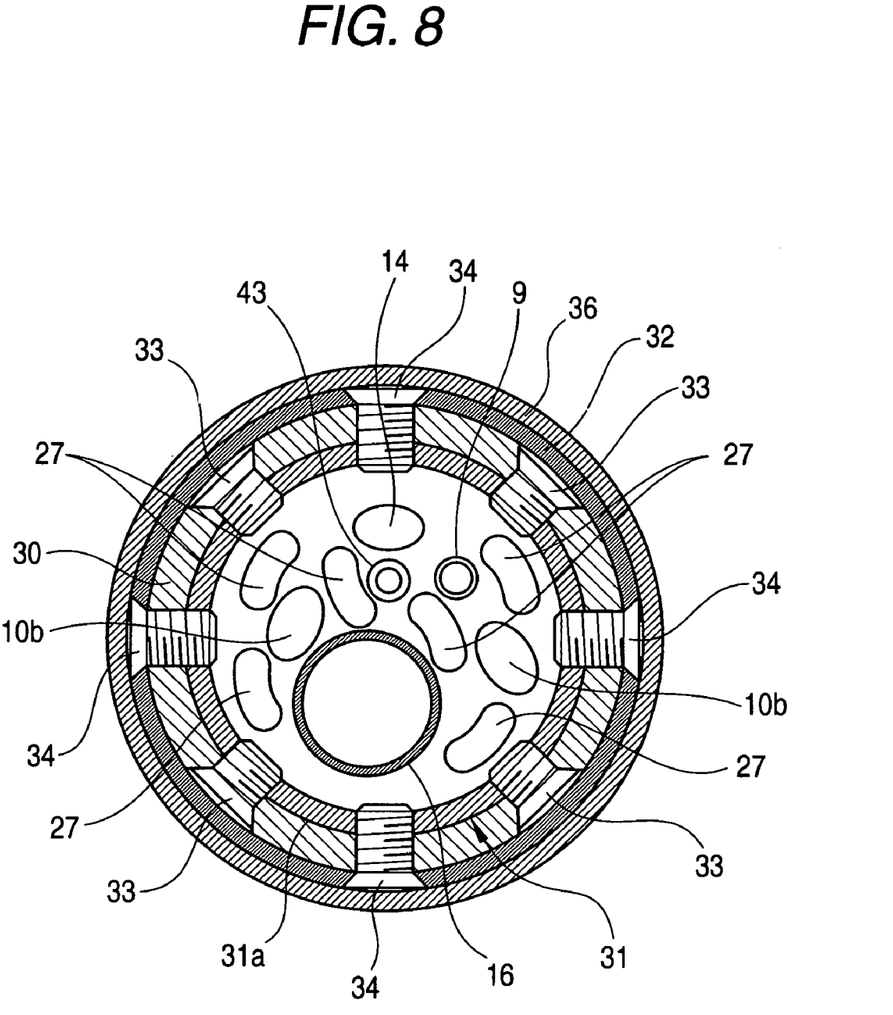
FIG. 8 is a sectional view along line D-D of FIG. 4.

The endoscopic observation section is structured in this way. The forward end of each member that constitutes the endoscopic observation section is firmly held by an endoscope attaching member 18. The endoscope attaching member 18 is made of a metallic material, such as stainless steel, having a plurality of through-holes through which each member constituting the endoscopic observation section is passed. A forward end cap 19 is fitted to the endoscope attaching member 18. The forward end cap 19 prevents the endoscope attaching member 18 made of the metallic material from being exposed to the outside. The endoscope attaching member 18 and the forward end cap 19 constitute a forward end block. As shown in FIG. 5, the forward end cap 19 has two threaded holes 19a in its thickness direction. Setscrews 20 are screwed into the threaded holes 19a, respectively, and the forward end of the setscrew 20 is pressed against the endoscope attaching member 18. In addition, a contact surface of the endoscope attaching member 18 and a contact surface of the forward end cap 19 are bonded together, whereby the forward end block made up of the endoscope attaching member 18 and the forward end cap 19 is unified.

A mechanism to perform an ultrasonic examination including a scan surface in the radial direction is provided at a position on the proximal end side of the forward end cap 19 of the distal hard part 2c. As is apparent from FIG. 6, this mechanism is made up of an array of a large number of ultrasonic vibrators arranged in a circumferential direction. The ultrasonic vibrators 21 are arranged in the form of a circle or a circular arc (for example, an angle of 270 degrees or more) so as to perform electronic scanning. A backing layer 22 is mounted on the inner circumference side of the ultrasonic vibrators 21 arranged in this way, and a sound lens 23 is mounted on the outer circumference side thereof. The ultrasonic vibrators 21, the backing layer 22, and the sound lens 23 constitute an ultrasonic transducer 24.

Each ultrasonic vibrator 21 has two electrodes 25 and 26. The electrode 25 that is one of the two electrodes is a common electrode 25 shared among all of the ultrasonic vibrators 21 (or among each set of a predetermined number of ultrasonic vibrators 21), whereas the other electrode 26 is individually used for each ultrasonic vibrator 21. The individual electrode 26 of the ultrasonic vibrators 21 is connected to wires 27. For this reason, flexible boards 28 and 29 are connected to the front and the rear of the ultrasonic transducer 24, respectively. The wires 27 are electrically connected to wiring patterns formed on the flexible boards 28 and 29. On the other hand, what is needed for the common electrode 25 is to be connected to at least one wire. For this reason, the common electrode 25 is connected to either the flexible board 28 or the flexible board 29.

The ultrasonic transducer 24 is shaped roughly like a cylinder. The inner circumferential surface of the ultrasonic transducer 24 serves as a tunnel-like passage. Each member that constitutes the endoscopic observation section is inserted into the inside of the tunnel-like passage by the ultrasonic transducer 24, and is positioned closer to the forward end than the ultrasonic transducer 24, and is fixed to the endoscope attaching member 18 covered with the forward end cap 19. The distal end of the ultrasonic transducer 24 is in contact with the end surface of the forward end cap 19, and the proximal end thereof is in contact with the end surface of the connection member 30. The connection member 30 forms a connection part to the angle part 2b in the distal hard part 2c.

Further, a bridging member 31 is provided inside a connecting member 30. A forefront ring 32 in an angle ring that forms the structure of the angle part 2b is connected to the connecting member 30 and the bridging member 31. For this reason, as is apparent from FIG. 8, the connecting member 30 and the bridging member 31 are connected together by a plurality of screws 33, and the forefront ring 32 is connected to these members by a plurality of screws 34.

Figure 9:
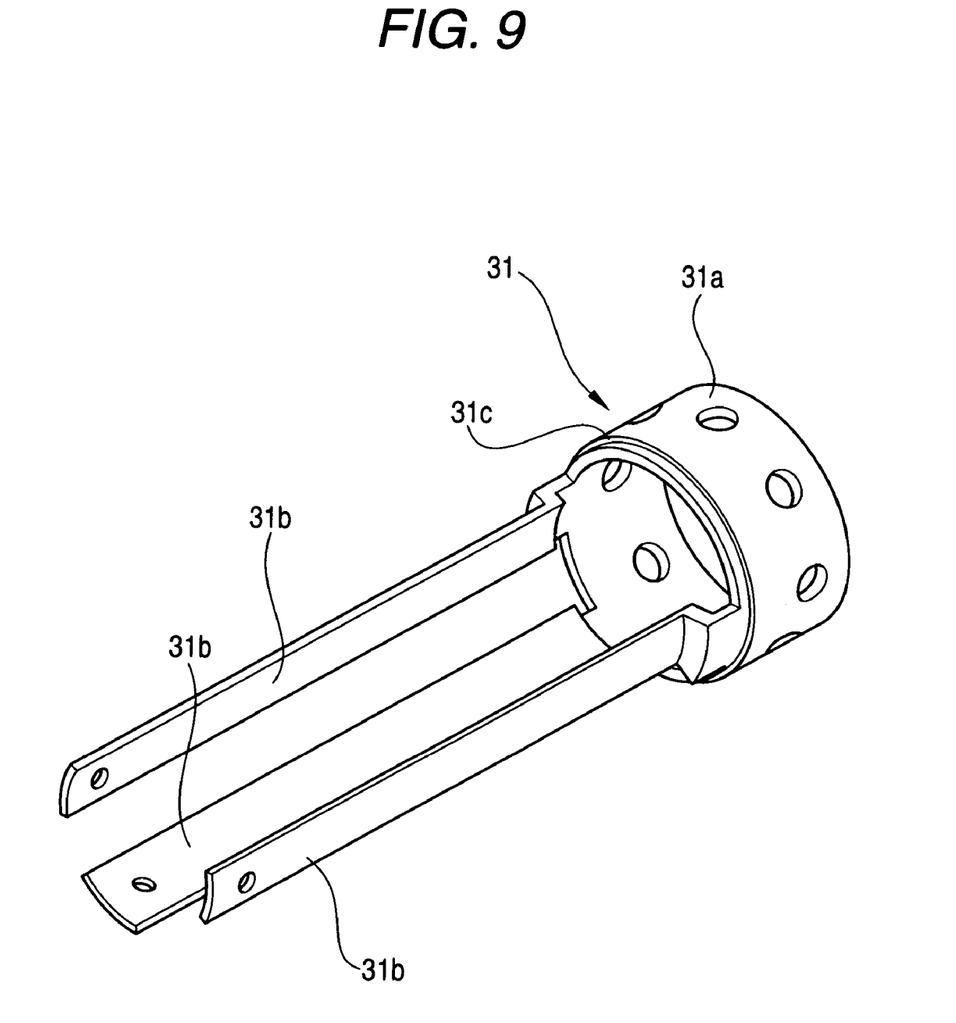
FIG. 9 is an external perspective view of a bridging member.

The bridging member 31 can fulfill the function of connecting a top ring 32 occupying the forefront position of the angle part 2b together with the connecting member 30 disposed closest to the proximal end in the distal hard part 2c, the function of positionally restricting the ultrasonic transducer 24 in a direction perpendicular to the axial line of the distal hard part 2c, and the function of forming a connection to a combination of the endoscope attaching member 18 and the forward end cap 19. Therefore, the bridging member 31 is required to have high strength, and is made of a metal, such as stainless steel, because the bridging member 31 is not exposed to the outside. As shown in FIG. 9, a part of the bridging member 31 that is connected to the connecting member 30 and to the forefront ring 32 of the angle part 2b by the screws 33 and 34 is a cylindrical part 31a. A plurality of connecting arms 31b (in this embodiment, three arms) are extended toward the forward end from this cylindrical part 31a.

The ultrasonic transducer 24 is positioned in the direction perpendicular to the axial line by being fitted to the connecting arm 31b. The forward end of each connecting arm 31b and the endoscope attaching member 18 are connected together by the screw 35. A step (i.e., a difference in level) 31c is formed on the outer circumferential surface of the cylindrical part 31a of the bridging member 31. This step 31c makes the diameter on the proximal end side larger. Further, a step 30a is formed on the inner circumferential surface of the connecting member 30. This step 30a makes the diameter of the inner circumferential surface on the proximal end side larger. The ultrasonic transducer 24 is sandwiched between the forward end cap 19 and the connecting member 30 by joining the step 31c and the step 30a together. Both end surfaces of the ultrasonic transducer 24, the proximal end surface of the forward end cap 19, and the distal end surface of the connecting member 30 are bonded together, and, as a result, the ultrasonic transducer 24 is positioned in the direction of the axial line and is prevented from being moved, and hence the ultrasonic transducer 24 is fixedly held at a predetermined position. An outer hull layer 36 of the angle part 2b is extended to an outer-circumferential-surface part on the proximal end side of the connecting member 30. The forward end of the outer hull layer 36 is fixed to the connecting member 30 of the distal hard part 2c by a fixing mechanism 37 made up of a spool and an adhesive.

In the ultrasonic endoscope, ultrasonic waves are sent toward the body from each ultrasonic vibrator 21 that constitutes the ultrasonic transducer 24, and reflection echoes emitted from a sectional region of tissues in the body are received. To restrain the attenuation of the ultrasonic waves sent and received in this way, annular concave grooves 40 and 40 are provided at positions before and behind the attaching member of the ultrasonic transducer 24, i.e., on the outer circumferential surface of the forward end cap 19 and the outer circumferential surface of the connecting member 30, respectively. As is apparent from FIG. 2, a balloon 41 that is filled and inflated with an ultrasonic wave transmission medium is attached between both annular concave grooves 40 and 40. This balloon 41 is made of a cylindrical, flexible film 41a. Fixed rings 41b, which are fixed to the annular concave grooves 40, are respectively provided on both ends of the flexible film 41a. The fixed ring 41b is fixed so that a tightening force acts on the annular concave groove 40. A supply/drain path 42 used to supply and drain the ultrasonic wave transmission medium into the balloon 41 is bored in the connecting member 30. A tube 43 is connected to the supply/drain path 42.

With the structure formed in this way, the insertion portion 2 is inserted into the body cavity of a subject. Thereafter, illumination light is projected from the lighting portion 10 that forms the endoscopic observation section into the body cavity, and an image of the body cavity is formed on a solid-state image pickup element 13 by the objective lens 12 attached to the observation portion 11. Thereafter, a video signal of the body cavity is obtained by the solid-state image pickup element 13, and is sent to the video signal processor. In the video signal processor, predetermined signal processing is performed, and the image of the body cavity is displayed on a monitor for displaying endoscopic images. Therefore, an endoscopic examination concerning the state of the body cavity can be performed by watching the monitor.

If a region of interest, such as a diseased part, is found as a result of this endoscopic examination, the ultrasonic transducer 24 is moved to the position facing this region of interest. In other words, the ultrasonic transducer 24 is placed at the position facing the region of interest by advancing the insertion portion 2 by a predetermined distance. An ultrasonic wave transmission medium is then supplied into the balloon 41, so that the flexible film 41a is expanded and brought into close contact with the inner wall of the body cavity. In this state, the ultrasonic vibrators 21 that form the ultrasonic transducer 24 and that are arranged in the circumferential direction are sequentially operated to send an ultrasonic pulse toward the body and receive a reflection echo thereof. Herein, some of the ultrasonic vibrators 21 are operated with a predetermined delay although the ultrasonic vibrators 21 can be operated sequentially one by one. Accordingly, for example, electronic focusing can be performed. Since a method in which a large number of ultrasonic vibrators 21 arranged as above are subjected to electronic scanning is known in the related art, a description of this method is omitted.

A reflection echo signal obtained by each ultrasonic vibrator 21 that constitutes the ultrasonic transducer 24 in this way is sent to the ultrasonic wave observation device by the connector 3c of the universal cord 3 through the wires 27 (which are bundled in the middle thereof), and is subjected to signal processing by the ultrasonic wave observation device. As a result, tomographic information concerning the state of the bodily tissues including the region of interest is obtained. This ultrasonic tomographic image is then displayed on the monitor attached to the ultrasonic wave observation device. As a result, for example, diagnosis of whether a diseased part is included in the tissues can be performed.

By the way, the ultrasonic vibrators 21 large in number and the wires 27 are electrically connected together through the flexible boards 28 and 29. These flexible boards 28 and 29 are disposed in such a way as to be sandwiched between the ultrasonic vibrator 21 and the backing layer 22. The flexible board 28 is extended toward the proximal end of the ultrasonic transducer 24, and the flexible board 29 is disposed on the distal end of the ultrasonic transducer 24.

Figure 10:
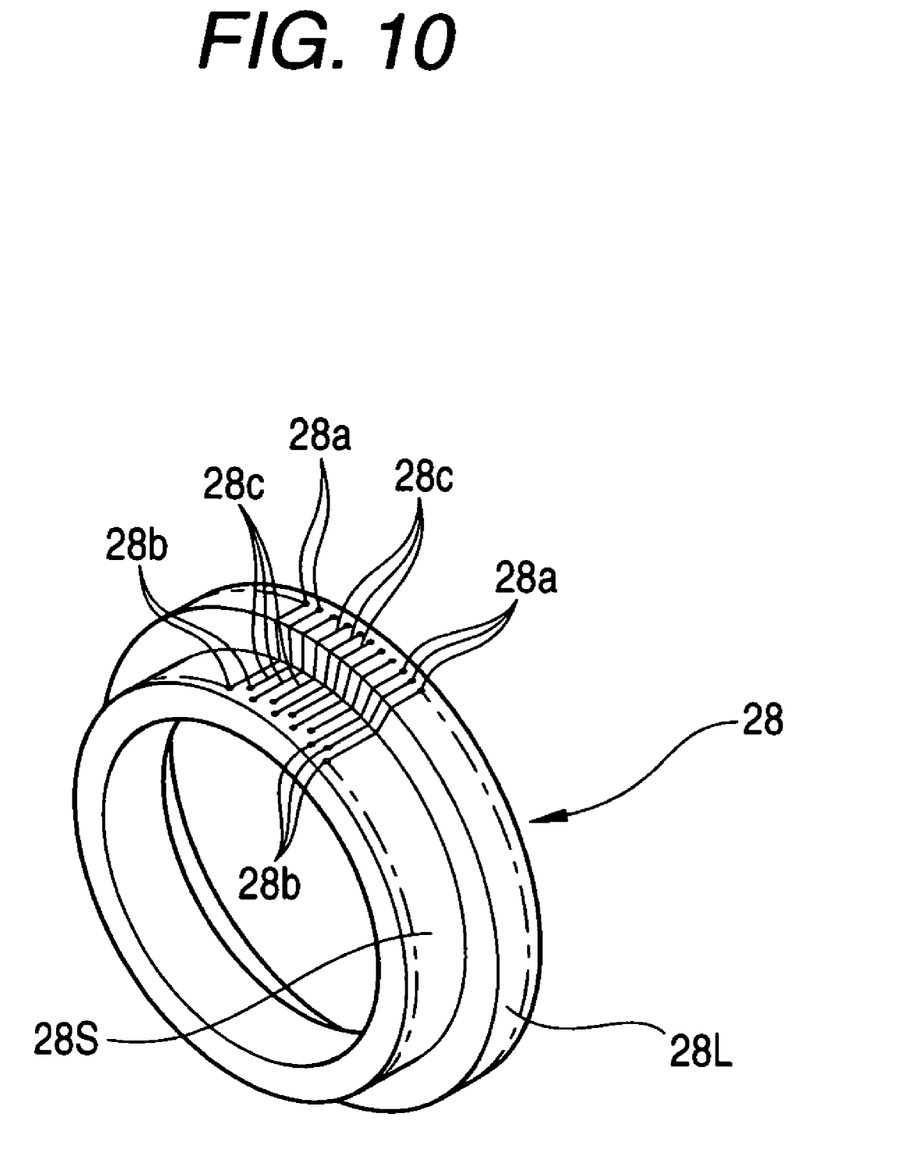
FIG. 10 is an explanatory view that shows a structure of a flexible board on the proximal end side.
Figure 11:
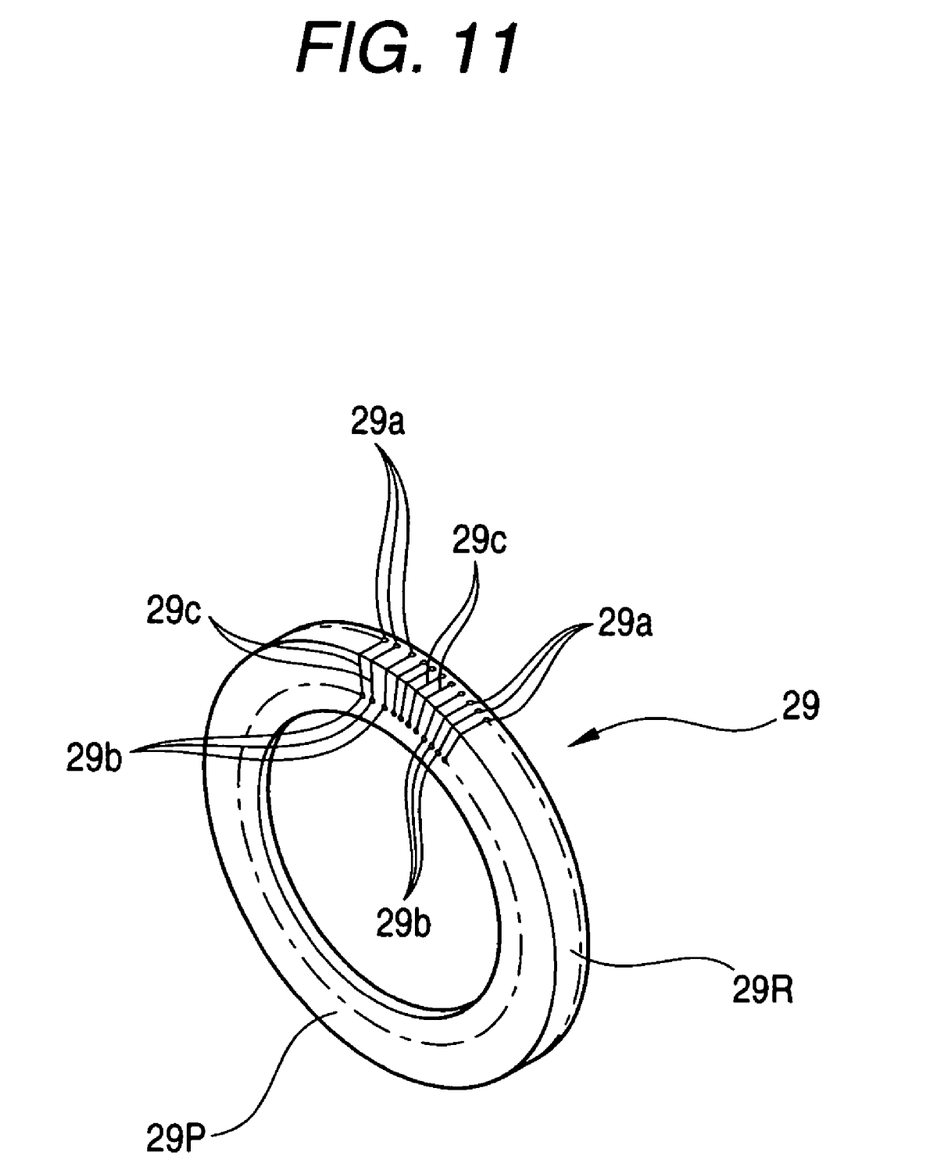
FIG. 11 is an explanatory view that shows a structure of a flexible board on the distal end side.

Next, the flexible board 28 is shown in FIG. 10, and the flexible board 29 is shown in FIG. 11. As is apparent from these figures, necessary wiring patterns are formed on the flexible boards 28 and 29 by, for example, a printing section. The wiring pattern is made up of first terminal parts 28a and 29a electrically connected to the individual electrodes 26, respectively, of the ultrasonic vibrator 21, second terminal parts 28b and 29b electrically connected to the wires 27 by, for example, a soldering section, and wires 28c and 29c through which the first and second terminal parts are connected together.

These flexible boards 28 and 29 are incorporated into the distal hard part 2c in the shape of a cylinder as a whole. A part on the side of which the first terminal parts 28a and 29a are disposed is interposed between each ultrasonic vibrator 21 that constitutes an array of ultrasonic vibrators annularly arranged and the backing layer 22. On the other hand, parts at which the second terminal parts 28b and 29b of the flexible boards 28 and 29 are disposed are respectively extended to the proximal end side and the distal end side of the ultrasonic transducer 24.

As is apparent from FIG. 10, the flexible board 28 extended to the proximal end of the ultrasonic transducer 24 has a large-diameter part 28L and a small-diameter part 28S by both of which a step (i.e., a difference in level) is formed. An extension part 22a is formed on the proximal end side of the backing layer 22 closer to the proximal end than the ultrasonic vibrator 21. As is apparent from FIG. 4, the large-diameter part 28L of the flexible board 28 is interposed between the ultrasonic vibrator 21 and the backing layer 22. The small-diameter part 28S of the flexible board 28 is joined to the extension part 22a. The second terminal part 28b is formed at the position of the small-diameter part 28S located on the extension part 22a. The wire 27 is connected to this location, and is extended from this connection part to the side of the angle part 2b through the inside of the connecting member 30. Herein, the bridging member 31 is connected to the connecting member 30. The connecting arm 31b of the bridging member 31 is extended to the distal end through the inside of the backing layer 22. Therefore, the wires 27 are guided inside the bridging member 31 in such a manner as to avoid the plurality of connecting arms 31b, and are bundled into a single group of wires or into a plurality of groups of wires. Therefore, in the figures, reference numeral 27 is given also to the bundled wires 27.

As is apparent from FIG. 11, the flexible board 29 located on the distal end side of the ultrasonic transducer 24 includes a cylindrical part 29R and an annular part 29P. The cylindrical part 29R is interposed between the ultrasonic vibrator 21 and the backing layer 22. The annular part 29P is joined to the end surface of the backing layer 22. The first terminal part 29a is formed on the cylindrical part 29R, and the second terminal part 29b is formed on the annular part 29P. Therefore, the wires 27 are connected at the position of the annular part 29P of the flexible board 29. The wires 27 change its direction at a gap between the ultrasonic transducer 24 and the forward end block made up of the endoscope attaching member 18 and the forward end cap 19, and are bundled into a plurality of groups of wires. The thus bundled wires 27 are passed through the tunnel-like passage inside the ultrasonic transducer 24, and are extended toward the angle part 2b. In this case, it is preferable to seal the connection part to the flexible board 29 of the wires 27 with resin.

Figure 12:
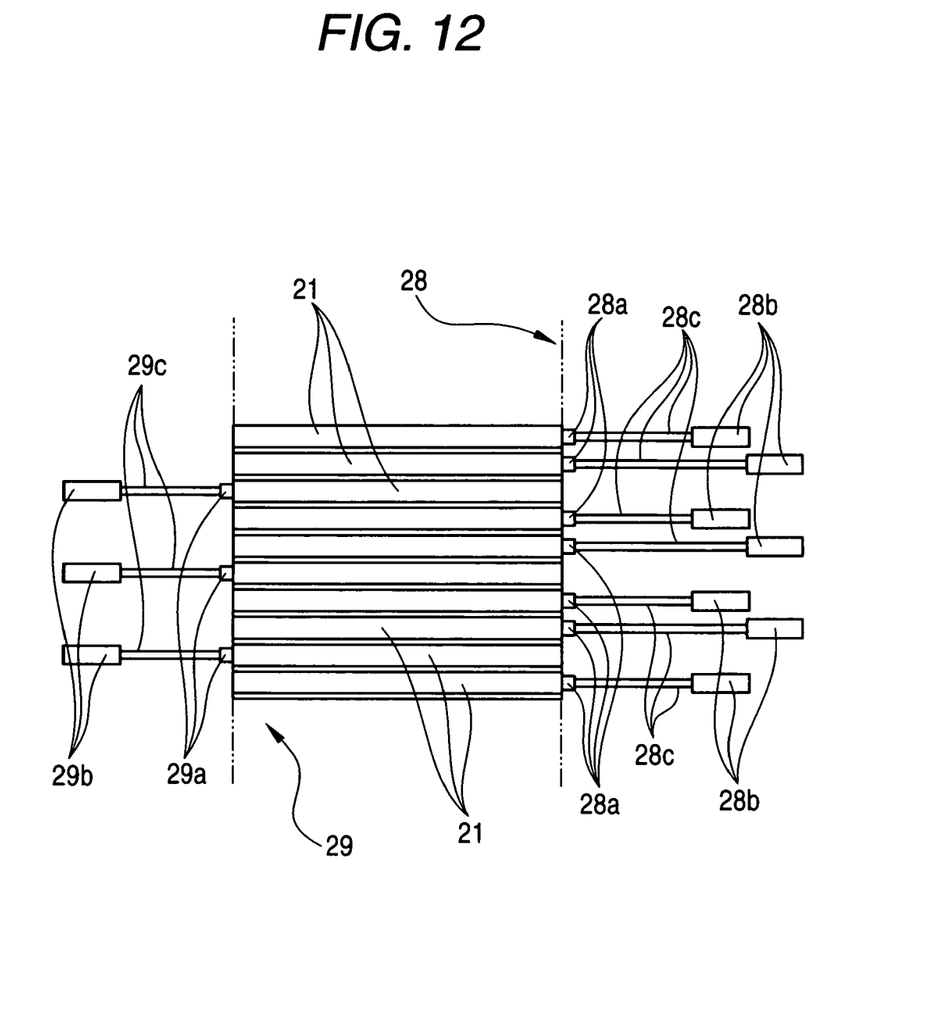
FIG. 12 is an explanatory view that schematically shows the wire connection part of each flexible board on the proximal and distal end sides with respect to an ultrasonic vibrator.

As described above, the wires 27 connected to the large number of ultrasonic vibrators 21 that constitute the ultrasonic transducer 24 are distributed into the proximal end side and the distal end side. This distribution ratio can be set at the ratio of 2 of the proximal end side to 1 of the distal end side as shown in FIG. 12. The second terminal parts 28b and 29b of the flexible boards 28 and 29 provided on the proximal and distal end sides can be enlarged by zigzag arranging the second terminal parts 28b provided on the flexible board 28 on the proximal end side. Therefore, the wires 27 connected by soldering can be firmly fixed. At this time, solder never overflows so as to short-circuit with other terminal parts.

The distribution of the wires 27 into both of the flexible boards 28 and 29 can be appropriately set in consideration of, for example, the position of the connecting arm 31b of the bridging member 31 disposed inside the flexible boards 28 and 29 or the position of each member that constitutes the endoscopic observation section. The distribution ratio can be set not at the ratio of 2:1 mentioned above but at an arbitrary distribution ratio. The flexible board 29 connected to the distal end side may be formed such that another cylindrical part is consecutively formed at the forward end of the annular part 29P, and the cylindrical part extended in this way is bonded with the inner surface of the backing layer 22 in the ultrasonic transducer 24 that forms the tunnel-like passage, and is connected to the wire 27 at the position of the proximal end of the backing layer 22.

The interval between the wire connection parts formed on the flexible boards can be widened by employing the foregoing structure, and the wire-connecting operation can be easily performed. Additionally, advantageously, the wires can be firmly fixed, and hence there is no fear that a short circuit or the like will be caused.

The entire disclosure of each and every foreign patent application from which the benefit of foreign priority has been claimed in the present application is incorporated herein by reference, as if fully set forth.

What is claimed is:

1. An ultrasonic endoscope comprising
an insertion portion comprising:
an angle part;
a distal hard part;
a cylindrical body that connects the angle part and the distal hard part;
an ultrasonic transducer backing plate formed annularly;
an endoscopic observation section attaching portion including a lighting portion and an observation portion, the lighting portion and the observation portion passing through an inside of the ultrasonic transducer backing plate and facing a front edge surface of the distal hard part;
an ultrasonic transducer in which a plurality of ultrasonic vibrators are arranged in a cylindrical shape or in an arcuate shape so as to perform ultrasonic electronic scanning in a circumferential direction, the ultrasonic transducer being attached to the ultrasonic transducer backing plate, the ultrasonic transducer having a distal end side facing the front edge surface of the distal hard part and having a proximal end side facing away from the front edge surface of the distal hard part;
a first flexible board connected to the distal end side of the ultrasonic transducer backing plate,
a second flexible board connected to the proximal end side of the ultrasonic transducer backing plate,
wherein the first flexible board comprises connection parts to electrodes of ones of the ultrasonic vibrators,
the second flexible board comprises connection parts to electrodes of the other ones of the ultrasonic vibrators,
each of the first and second flexible boards comprises a predetermined number of wire connection parts,
wires are connected to each of the wire connection parts,
those of the wires connected to the second flexible board are extended, and
the first flexible board or those of the wires connected to the first flexible board are extended toward the angle part through a hollow part of the ultrasonic transducer backing plate, and after a wire of a tip end of the distal end side passes through the hollow part of the ultrasonic transducer once, the wire is disposed to change a direction thereof.

2. The ultrasonic endoscope according to claim 1,
wherein the second flexible board is greater in number of the connection parts to the electrodes of the ultrasonic vibrators than the first flexible board.

3. The ultrasonic endo scope of claim 1, wherein
the first flexible board and the second flexible board comprise wiring patterns, each wiring pattern having one end connected to the wire connection parts.

4. The ultrasonic endo scope of claim 1, wherein
the first flexible board includes a cylindrical part and an annular part, and the second flexible board includes a large-diameter part and a small-diameter part forming a step therebetween.

* * * * *